(12) United States Patent
Temple (10) Patent No.: US 9,907,461 B2
(45) Date of Patent: Mar. 6, 2018

(54) HEATER FOR SURGICAL VIEWING INSTRUMENTS

(71) Applicant: John Temple, Chelsea, MI (US)

(72) Inventor: John Temple, Chelsea, MI (US)

(*) Notice: Subject to any disclaimer, the term of this patent is extended or adjusted under 35 U.S.C. 154(b) by 0 days.

(21) Appl. No.: 15/151,645

(22) Filed: May 11, 2016

(65) Prior Publication Data

US 2016/0324411 A1 Nov. 10, 2016

Related U.S. Application Data

(63) Continuation-in-part of application No. 12/471,895, filed on May 26, 2009, which is a continuation-in-part of application No. 10/827,493, filed on Apr. 19, 2004, now Pat. No. 7,537,563.

(60) Provisional application No. 60/463,642, filed on Apr. 17, 2003.

(51) Int. Cl.
*A61B 1/06* (2006.01)
*A61B 1/12* (2006.01)
*A61B 50/00* (2016.01)
*G02B 27/00* (2006.01)
*A61B 1/00* (2006.01)
*A61B 1/313* (2006.01)

(52) U.S. Cl.
CPC .......... *A61B 1/127* (2013.01); *A61B 1/00144* (2013.01); *A61B 1/128* (2013.01); *A61B 50/00* (2016.02); *G02B 27/00* (2013.01); *A61B 1/313* (2013.01); *A61B 2050/0017* (2016.02)

(58) Field of Classification Search
USPC ................................ 600/101–102, 133, 169
See application file for complete search history.

(56) References Cited

U.S. PATENT DOCUMENTS

| | | | | | |
|---|---|---|---|---|---|
| 3,463,161 | A | * | 8/1969 | Andrassy | A61F 7/02 126/400 |
| 4,077,390 | A | * | 3/1978 | Stanley | A61F 7/03 126/263.04 |
| 5,205,278 | A | * | 4/1993 | Wang | A61F 7/03 126/204 |
| 5,351,675 | A | * | 10/1994 | Brodsky | A61B 1/127 126/263.08 |
| 5,651,757 | A | * | 7/1997 | Meckstroth | A61B 1/127 600/101 |
| 5,805,766 | A | * | 9/1998 | Wang | F24J 1/00 126/263.01 |
| 5,910,106 | A | * | 6/1999 | Morgan | A61B 1/00131 126/263.05 |

(Continued)

*Primary Examiner* — Matthew J Kasztejna
(74) *Attorney, Agent, or Firm* — John G. Posa; Belzer PC (57) ABSTRACT

A system and associated method are used for warming an endoscope, laparoscope, or other such instrument to minimize fogging. A flexible pad has a length, a width and a periphery for wrapping around the instrument. An activation disc and a mixture of water and sodium acetate are used to generate heat through an exothermic reaction initiated through manual manipulation of the disc. The disc may be exposed in a flexible tab in fluid communication with the pad. A housing includes an end bore to receive the instrument such that the instrument is surrounded by the folded or rolled pad within the housing. The housing may further include a slit or narrow opening enabling the tab and activation disc to extend therethrough and outside the housing for activation.

11 Claims, 10 Drawing Sheets

(56) References Cited

U.S. PATENT DOCUMENTS

| | | | |
|---|---|---|---|
| 6,234,635 B1* | 5/2001 | Seitzinger | A61B 1/127 359/512 |
| 2002/0022762 A1* | 2/2002 | Beane | A61B 1/122 600/101 |

* cited by examiner

HEATER FOR SURGICAL VIEWING INSTRUMENTS

REFERENCE TO RELATED APPLICATIONS

This application is a continuation-in-part of U.S. patent application Ser. No. 12/471,895, filed May 26, 2009, which is a continuation-in-part of U.S. patent application Ser. No. 10/827,493, filed Apr. 17, 2003, now U.S. Pat. No. 7,537,563, which claims priority from U.S. Provisional Patent Application Ser. No. 60/463,642, filed Apr. 17, 2003. The entire content of each application is incorporated herein by reference.

FIELD OF THE INVENTION

This invention relates generally to surgical instruments and supplies and, in particular, to heater for medical and surgical viewers subject to fogging.

BACKGROUND OF THE INVENTION

In minimally invasive surgical (MIS) procedures, elongated illuminators and viewers, i.e., laparoscopes and endoscopes, are inserted through small incisions in the abdominal wall or elsewhere. The viewer is typically coupled to a video camera that shows the operating field on a monitor.

A common problem is that the lens on the viewer becomes fogged. When the viewer is inserted, the lens is typically at operating room temperature which is often much colder than room temperature. The body cavity is at body temperature and high humidity. As such, water droplets condense on the lens, obscuring the view. When the lens fogs, the surgeon must remove the instrument, clean the lens, and reinsert the instrument at which time fogging often begins again.

To address this problem, the instrument may be immersed in a warm saline bath before surgery and during cleaning. This can be time-consuming and it is difficult to control temperature to consistent, effective working temperature.

An automated approach is described in Published U.S. Patent Application 2002/0022762 A1. A lens warming and cleaning device for use with an optical surgical instrument is disclosed. The device includes a heat-conducting tube sized and shaped to receive the lens portion of the instrument, a heating element thermally coupled to an exterior of the tube, and a cleaning member disposed within the tube. The cleaning member is disposed such that when the lens portion of the instrument is inserted into the tube, the lens portion contacts the cleaning member.

The heating element comprises a flexible pad that surrounds at least a portion of the tube including the lens portion. The pad may be wrapped around tube or attached to tube using an adhesive or hook-and-loop fasteners.

In one disclosed embodiment, the heating pad includes a flexible, air-permeable outer bag that encases a chemical mixture that generates an exothermic reaction when activated. The chemical mixture can be, e.g., a mixture of iron powder, water, cellulose, vermiculite, activated carbon, and salt. Exposing the mixture to atmospheric oxygen triggers an exothermic reaction that warms the pad to a temperature of about 60° C. and sustains that temperature for about six hours.

Other types of known exotheimic reaction mixtures can be used. For example, the mixture can consist of iron powder, a chloride or sulfate of a metal having a tendency of ionization greater than iron, active carbon, and water. Alternatively, the chemical mixture can be a super-cooled, supersaturated aqueous solution of sodium acetate. The pad can also employ other types of exothermic chemical reactions to generate heat, or it can include a resistance heater powered by, e.g., a battery or an external source of electricity.

The problems with this system are two-fold. First, the addition of a cleaning mechanism is all embodiments constitutes an unnecessary complication, since warming is by far the greatest need. Additionally, although "other types of exothermic chemical reactions" are mentioned in passing, activation methods and apparatus are not disclosed. Accordingly, the need remains for a less expensive yet effective endoscope/laparoscope warming system.

SUMMARY OF THE INVENTION

This invention resides in a system and associated method for warming an endoscope, laparoscope, or other such instrument to minimize fogging. The preferred embodiment comprises a flexible pad having a length, a width and a periphery for wrapping around the instrument and a plurality of separate chambers defined through partitions. Each of the separate chambers includes an activation disc and a mixture of water and sodium acetate to generate heat through an exothermic reaction initiated through manual manipulation of the disc for that chamber.

The pad is preferably made from two plastic sheets of substantially equal size, with the chambers being formed by heat-sealing or otherwise bonding the periphery of the sheets and the partitions. At least some of the partitions establish lengthwise and/or widthwise fold lines in the pad. At least one of the partitions may include a gap to facilitate fluid transfer of the mixture. In the preferred embodiments, the disc is made of perforated stainless steel.

In accordance with one preferred embodiment, the disc is disposed in a flexible peripheral tab in fluid communication with the sodium acetate solution, and the system includes a thermally insulated housing to receive the pad in a folded or rolled condition. The housing includes an end bore to receive the instrument such that the instrument is surrounded by the folded or rolled pad within the housing. The housing further includes a slit or narrow opening enabling the tab and activation disc to extend therethrough and outside the housing for activation. In one configuration the housing includes a body portion and an endcap that opens and closes to receive the pad in a folded or rolled condition, and the slit or narrow opening is situated between the body portion and the endcap enabling the tab and activation disc to extend therethrough and outside the housing.

BRIEF DESCRIPTION OF THE DRAWINGS

FIG. 16A is a cross section of pads applicable to the housing of FIGS. 14A-C showing multiple fluid chambers;

FIG. 19 is a plan view of an different warming pad applicable to the housing of FIGS. 14A-C;

DETAILED DESCRIPTION OF THE INVENTION

This invention improves upon the prior art by providing a low-cost yet effective heater for medical/surgical viewers subject to fogging, including endoscopes, laparoscopes, elongated microscopes, and so forth. Broadly, the apparatus includes a housing into which there is disposed a heating pad containing chemicals to produce heat through an exothermic reaction. The pad is rolled in the housing to create an elongated cavity in alignment with an aperture through the housing into which the instrument to be warmed is placed. In a preferred embodiment, a heat-conductive tube is also included between the rolled pad and instrument to provide for more consistent heating, and sodium acetate is used as the active ingredient in the pad, generated heat through contact with water also in the pad.

Figures 1, 2:
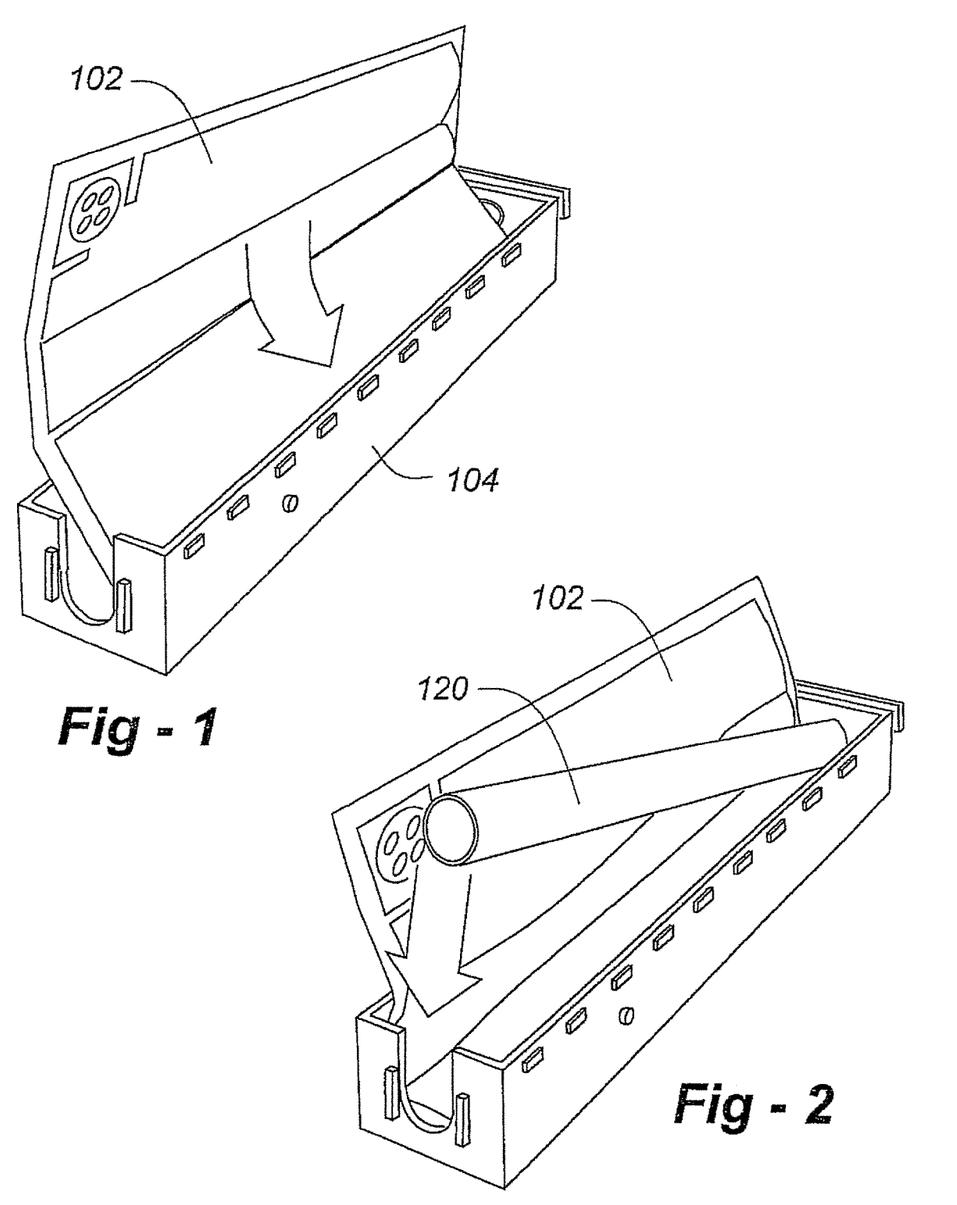
FIG. 1 is a drawing which shows the way in which a heating pad is inserted into a housing with the top cover removed.
FIG. 2 shows the way in which an internal tube is placed into the pad.

Now making reference to the drawings, FIG. 1 is an oblique representation showing the way in which pad 102 is placed into a housing 104 without a lid or hinged access panel, which will be described with reference to subsequent figures. In FIG. 2, a heat-conductive tube 120 of aluminum, stainless steel, or other suitable metal or other material is placed into the partially rolled pad 102.

Figures 3, 4:
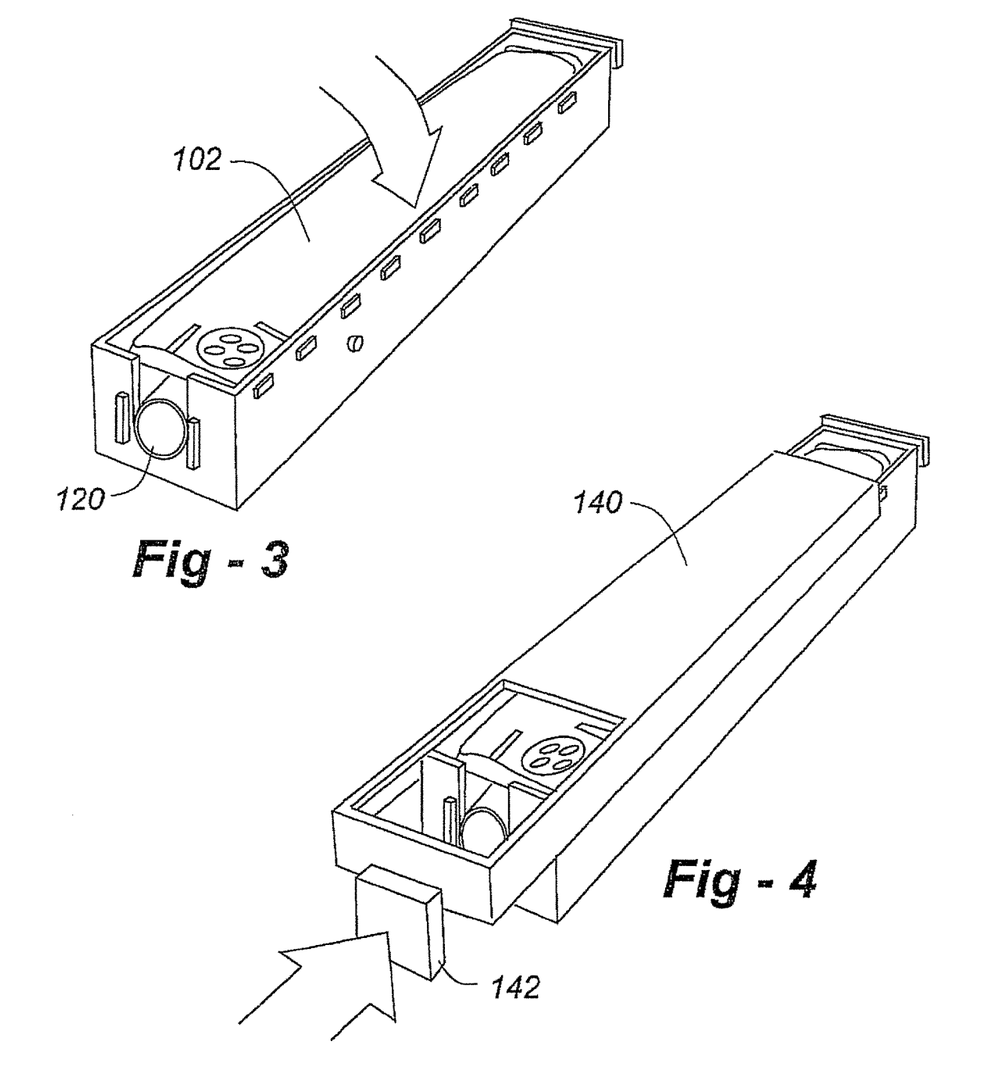
FIG. 3 is a drawing which shows how the pad is then folded over on top of the tube to completely surround it.
FIG. 4 illustrates the addition of the top cover without a hinge lid.
Figures 5, 6:
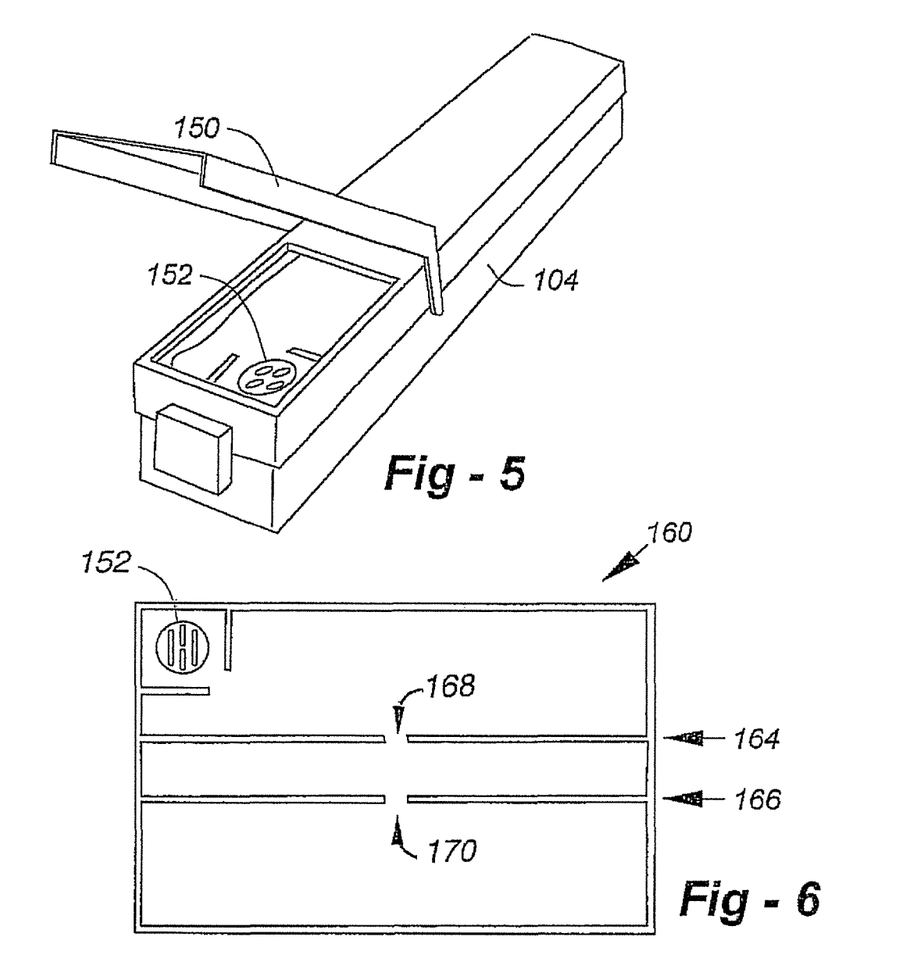
FIG. 5 is the drawing of a completed unit including a hinge lid.
FIG. 6 is a drawing of the preferred embodiment the pad.

In FIG. 3, the remaining portion of the pad 102 is folded over and onto the tube 120, again, without the lid or access panel being shown. In FIG. 4, the lid 140 is placed onto the housing, with an access door 142 being provided in alignment with the opening of tube 120, as shown. In FIG. 5, a hinged lid 150 is added, allowing a user to open the lid to gain access to an activation area 152 on the pad, which will be described in further detail below.

FIG. 6 is a plan view of a preferred heating pad 160 according to the invention. The pad contains a mixture of sodium acetate and water, and, unique to the invention, a particular spot 152 is provided, including a stainless steel disc to initiate the chemical reaction. Referring back to FIG. 5, this disc is placed on the pad so that when rolled into the housing, the area 152 is easily accessible when the hinged lid 150 is opened. Note that the pad 160 is also otherwise partitioned along lines 164 and 166 to conveniently provide fold areas for easier placement into the housing 104.

Figure 7:
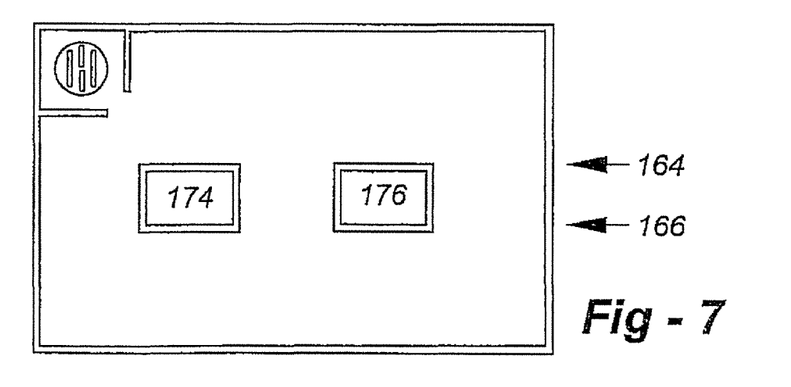
FIG. 7 is a drawing illustrating an alternative embodiment of a pad.

FIG. 7 illustrates an alternative design for the pad, wherein, instead of elongated seams 164 and 166, islands 174 and 176 are provided instead, these also being conducive to folding along the same desired line.

Figure 8:
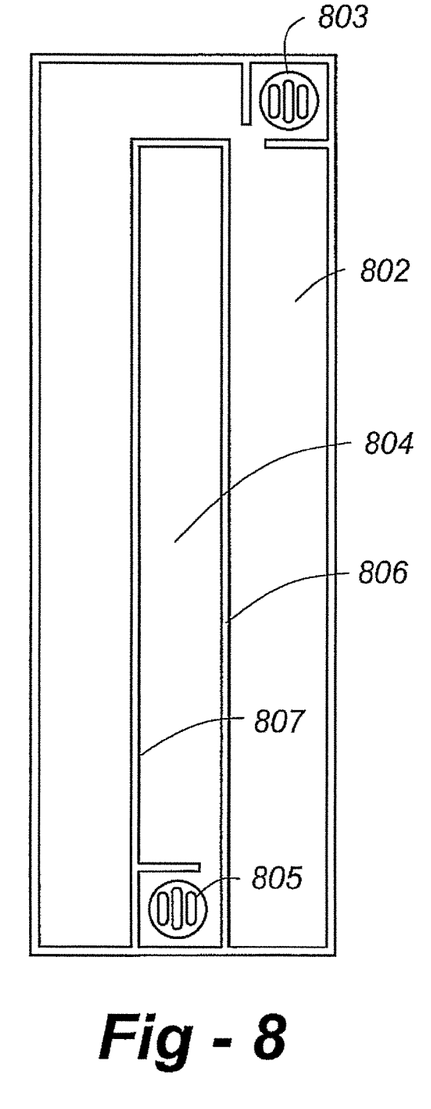
FIG. 8 is a drawing that depicts an alternative embodiment of the invention having a plurality of heatable chambers.
Figure 9:
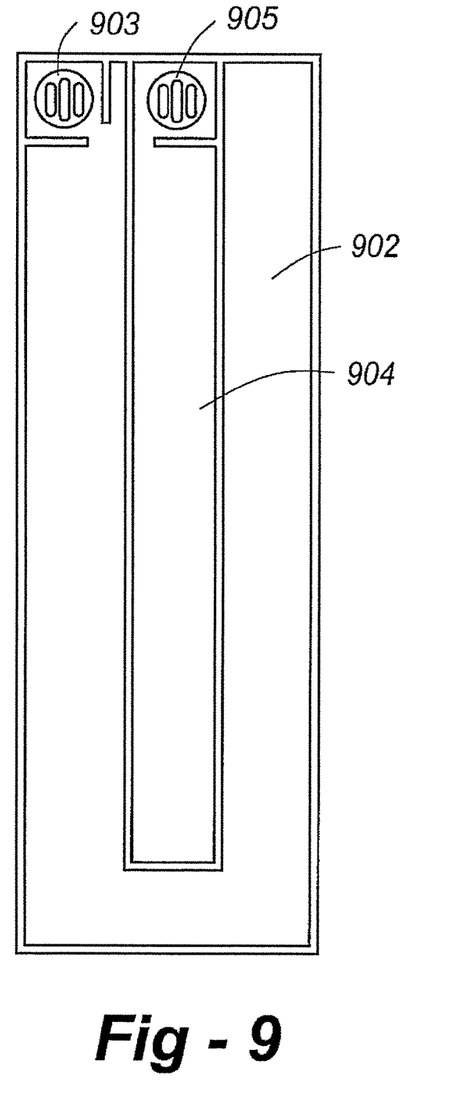
FIG. 9 depicts an alternative embodiment of the invention having a plurality of heatable chambers and activation discs at the same end.
Figure 10:
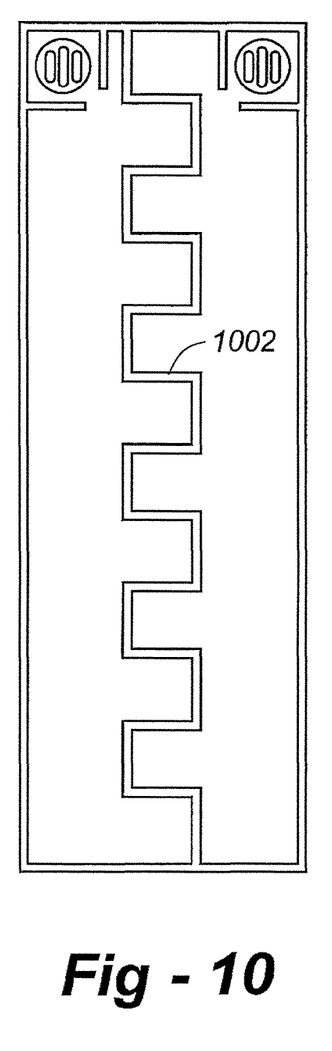
FIG. 10 shows an alternative embodiment of the invention having a plurality of heatable chambers in a different arrangement.
Figure 11:
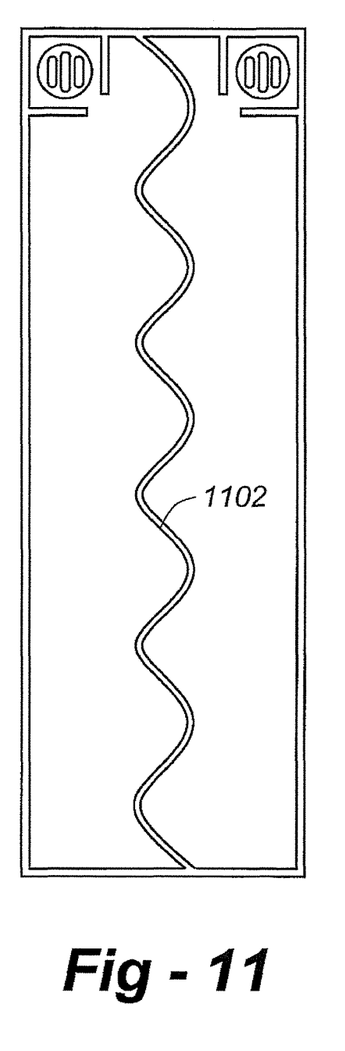
FIG. 11 shows an alternative embodiment of the invention having a plurality of heatable chambers in yet a further arrangement.

FIG. 8 is a drawing that depicts an alternative embodiment of the invention having a plurality of heatable chambers 802, 804 separated by sealed segments such as 806. Although two separate chambers are shown, more may be accommodated with appropriate seals. The activation disc for chamber 802 is shown at 803, whereas the disc for chamber 804 is shown at 805. The advantage of separate heatable chambers is that one chamber may be heated and used during a particular procedure and, if the procedure is sufficiently long, a different chamber may be heated for prolonged use. Note that in this and the embodiments which follow, sealed partitions such as 806, 807 may, or may not, double for use as fold lines. FIG. 9 depicts an alternative embodiment of the invention having a plurality of heatable chambers 902, 904 and activation discs 903, 905 at the same end;

FIG. 10 shows an alternative embodiment of the invention having a plurality of heatable chambers in a different arrangement, separated here with a meandering partition composed of straight segments. FIG. 11 shows an alternative embodiment of the invention having a plurality of heatable chambers in yet a further arrangement separated with a wavy partition 1102.

Figures 12, 13:
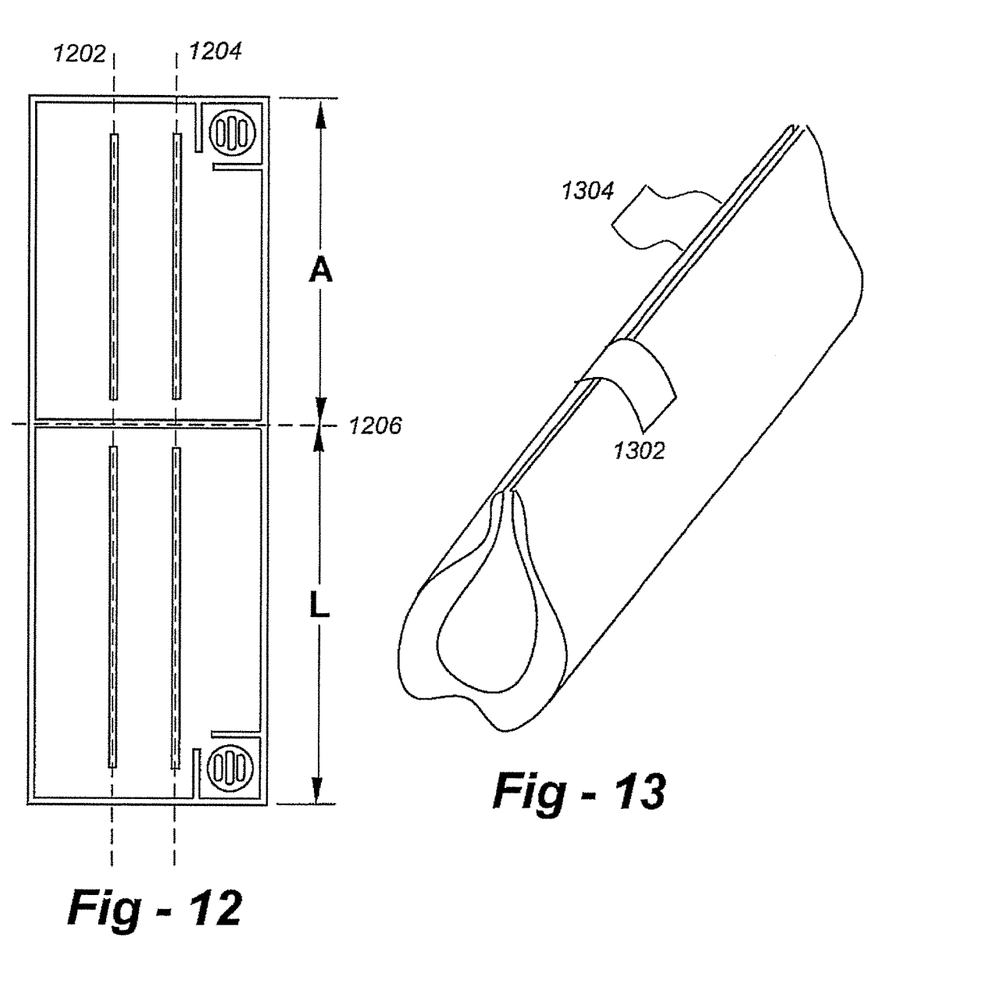
FIG. 12 shows an alternative embodiment of the invention having a plurality of heatable chambers with common fold lines.
FIG. 13 shows how one or more pieces of tape or other elements may be used to secure one edge of the pad to another once the pad is wrapped around an instrument to be warmed.

FIG. 12 shows an alternative embodiment of the invention having a plurality of heatable chambers with common fold lines 1202, 1204. A transverse fold line 1206 is also shown enabling the pad to form a pocket-like structure. The distances A and L may be the same of different. In all embodiments disclosed herein, the structure may be folded lengthwise (or widthwise in the case of FIG. 12), and secured with one or more pieces of tape 1302, 1304 or other fasteners such as hook-and-loop tabs, etc., as shown in FIG. 13.

Figures 14A, 14B, 14C:
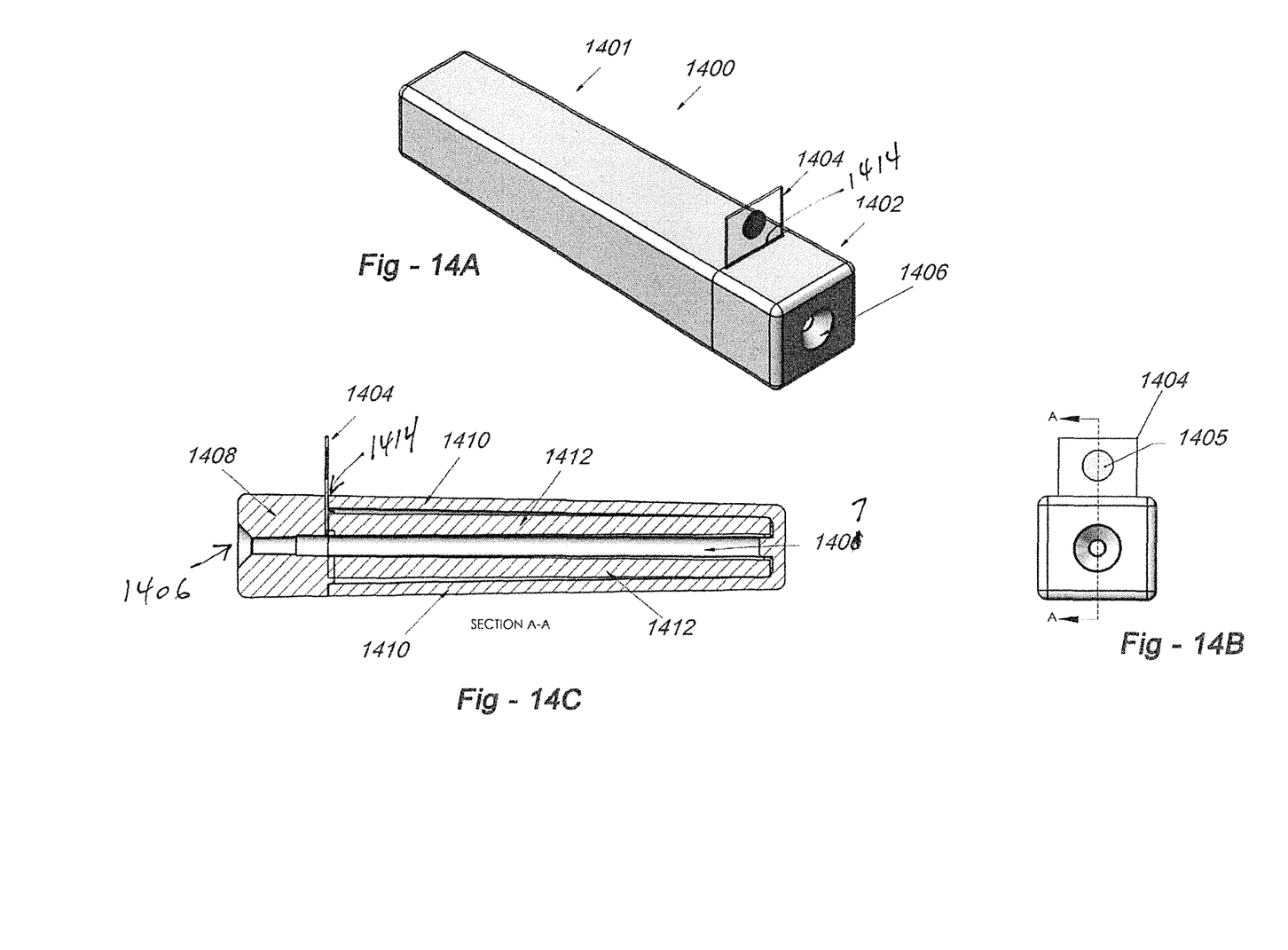
FIG. 14A is an oblique view of an alternative housing that enables activation of a heating pad with the housing in a closed configuration.
FIG. 14B is an end view of the housing of FIG. 14.
FIG. 14C is a side cross section of the housing of FIG. 14 taken along Section A-A.

One of the drawbacks of the housing of FIGS. 1-5 is that the access door or panel must be opened and closed to effectuate activation. FIG. 14A is an oblique view of an alternative housing 1400 that enables activation of a heating pad with the housing in a closed configuration. The housing includes a body portion 1401 and a removable/replaceable endcap portion 1408, but unlike the Housing of FIGS. 1-5, the activation disc 1404 may be activated when the housing closed with the instrument is inserted into port 1406. In addition to convenience, such a configuration minimizes cooling of the fluid due to ambient exposure.

FIG. 14B is an end view of the housing of FIG. 14, and FIG. 14C is a side cross section of the housing of FIG. 14 taken along Section A-A. The housing includes an outer plastic skin that encases foam insulation in regions 1408 and 1410. Numerical reference 1412 identifies the scope warmer pad 1412 rolled within the interior of the housing, thereby creating a bore 1407 to receive the scope through port 1406. When the cap is installed and the housing is closed, a tab 1404 containing activation disc 1504 extends through a slit or narrow opening 1414 allowing for activation of the disc outside of the warming device. Though not necessary to the invention, the tab is preferably bent so as to be generally perpendicular to the axis of the bore in the housing.

Figure 15:
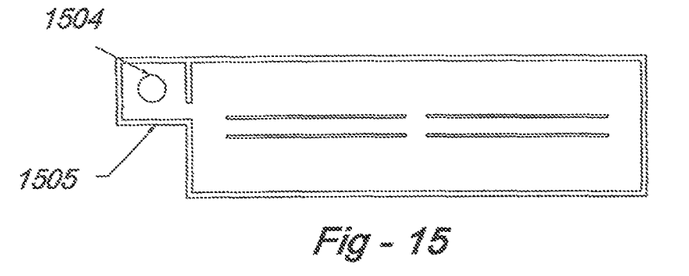
FIG. 15 is a plan view of a warming pad applicable to the housing of FIGS. 14A-C.
Figures 16A, 16B:
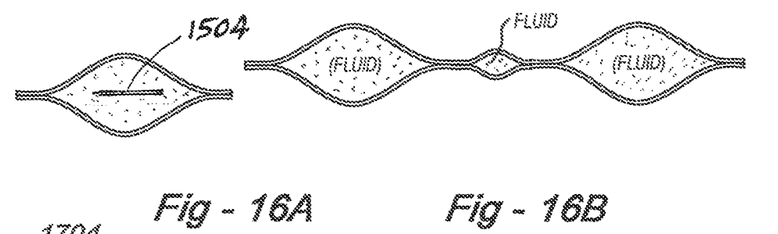
FIG. 16A is a cross section of pads applicable to the housing of FIGS. 14A-C including the activation disc.

FIG. 15 is a plan view of a warming pad applicable to the housing of FIGS. 14A-C. The tab is shown at 1505, and the disc is indicated at 1504. FIGS. 16A and 16B are cross sections showing the disc 1504 and sodium acetate fluid. As with the other embodiments disclosed herein, the bag itself is made of a thin, flexible plastic, preferably transparent enough to view the state of the sodium acetate as it changes state. The entire periphery of all of the bag embodiments is heat-sealed or otherwise bonded to maintain water-tightness. The other sets of double lines in the drawings are other sealed areas to assisted with folding, but note that in most instances the sealed lines do not extend to the edges to allow for fluid flow and activation of the entire fluid reservoir.

Figure 17:
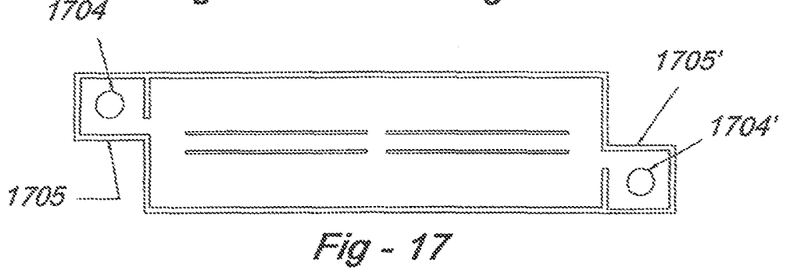
FIG. 17 is a plan view of an alternative warming pad applicable to the housing of FIGS. 14A-C.
Figure 18:
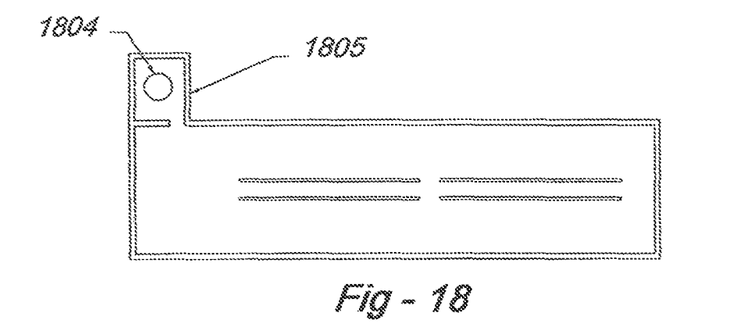
Figure 19:
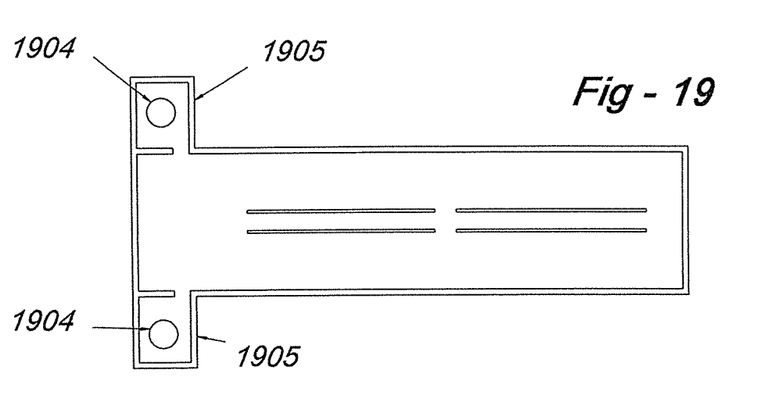
FIG. 19 is a plan view of a further alternative warming pad applicable to the housing of FIGS. 14A-C.
Figure 20:
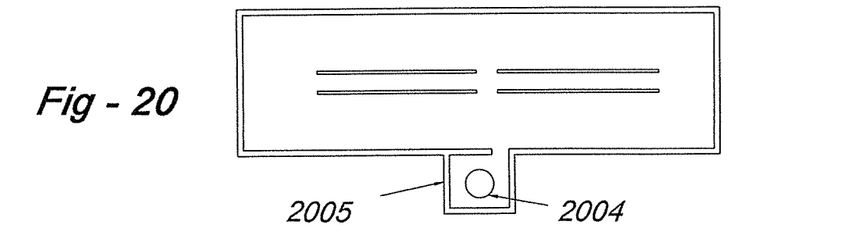
FIG. 20 is a plan view of yet a further alternative warming pad applicable to the housing of FIGS. 14A-C.

FIG. 17 is an alternative showing two sets of tabs 1705, 1705' and discs 1704, 1704' enabling installation in either direction. FIG. 18 show a side tab 1805 with disc 1804. With such a configuration would preferably use a more parallel passage through the housing as opposed to a transverse slit or opening. FIG. 19 illustrates a pair of opposing side tabs 1905, 1905' and discs 1904, 1904'. FIG. 20 shows that the tab 2005 and disc 2004 may be located at any area along the side of the pad proper.

Figures 21A, 21B:
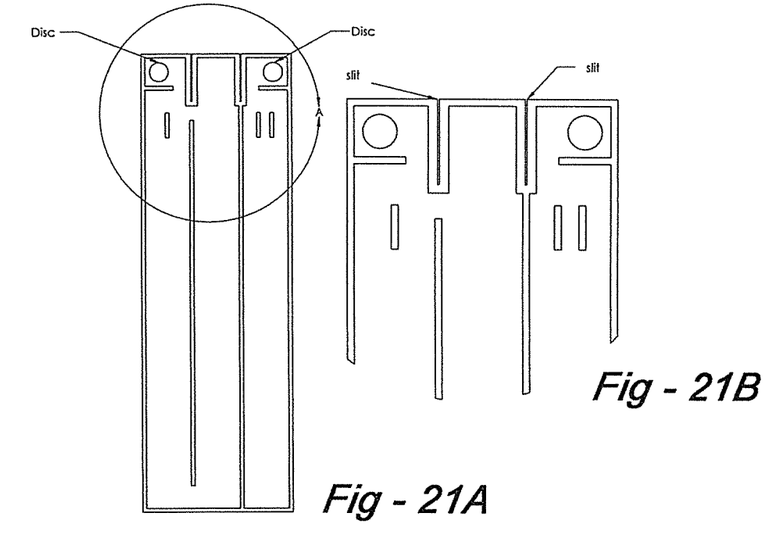
FIG. 21A is a plan view of yet a different warming pad applicable to the housing of FIGS. 14A-C.
FIG. 21B is a detail view of the warming pad of FIG. 21A showing the slits made into the article.
Figure 22:
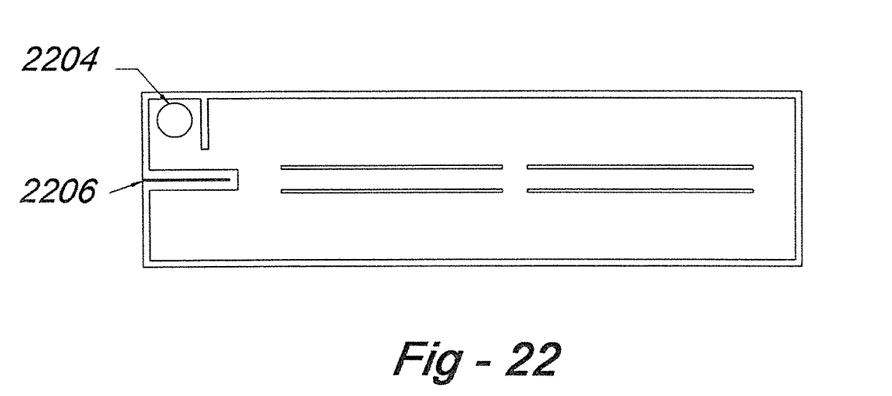
FIG. 22 is a plan view of yet a different alternative warming pad with a single slit.

FIGS. 21, 22 depict the use of slits to facilitate tab bending. Such slits may be formed before or after peripheral heat sealing to simplify manufacturing. Note in FIG. 21A that one of the internal seals 2120 does extend from end to end, such that the two discs may be used at the same or different times to heat chambers 2122, 2124.

The invention claimed is:

1. A system for warming an endoscope, laparoscope, or other such instrument to minimize fogging, comprising:
    a flexible pad having a seal periphery and filled with a sodium acetate solution;
    the flexible pad defining a plane in an unfolded state with a length and a width dimensioned to wrap around the instrument;
    an activation disc disposed in the sodium acetate solution causing the solution to generate heat through an exothermic reaction initiated through manual manipulation of the disc;
    wherein the disc is disposed in a flexible peripheral tab in fluid communication with the sodium acetate solution;
    the system further including a thermally insulated housing having an open condition to receive the pad in a folded or rolled condition, and a closed condition to contain the pad within the thermally insulated housing; and
    wherein the housing includes a slit or narrow, elongated opening enabling the tab and activation disc to extend therethrough, such that the tab and activation disc are outside the housing for activation when the housing is in the closed condition.

2. The system of claim 1,
    wherein the pad includes one or more partially sealed lines, each functioning as a fold line; and
    including at least one partially sealed line that includes at least one gap to facilitate fluid transfer.

3. The system of claim 2, wherein at least some of the sealed lines establish lengthwise fold lines in the pad.

4. The system of claim 2, wherein at least some of the sealed lines establish widthwise fold lines in the pad.

5. The system of claim 1, further including:
    one or more fully sealed lines within the pad to establish separate chambers within the pad; and
    an activation disc disposed with each separate chamber.

6. The system of claim 1, wherein:
    the pad is made from two overlying plastic sheets of substantially equal size; and
    the sheets are heat sealed around their peripheries.

7. The system of claim 1, wherein the activation disc is made of perforated stainless steel.

8. The system of claim 1, wherein the housing further includes an end bore to receive the instrument such that the instrument is surrounded by the folded or rolled pad within the housing.

9. The system of claim 1, wherein:
    the housing includes a body portion and an endcap that opens and closes to receive the pad in a folded or rolled condition.

10. The system of claim 9, wherein the housing further includes an end bore to receive the instrument such that the instrument is surrounded by the folded or rolled pad within the housing.

11. The system of claim 1, wherein the tab is formed with a slit in the pad.

* * * * *